United States Patent [19]

Maul et al.

[11] Patent Number: 5,047,584
[45] Date of Patent: Sep. 10, 1991

[54] PROCESS FOR THE PREPARATION OF PENTAHALOETHOXY BENZOYL HALIDE COMPOUNDS

[75] Inventors: James J. Maul, Grand Island, N.Y.; Byron R. Cotter, Northvale, N.J.

[73] Assignee: Occidental Chemical Corp., Grand Island, N.Y.

[21] Appl. No.: 806,915

[22] Filed: Dec. 9, 1985

[51] Int. Cl.$^5$ ............................................. C07C 51/60
[52] U.S. Cl. .................................. 562/852; 562/849; 562/474; 562/851
[58] Field of Search ..................... 260/544 F; 562/852

[56] References Cited

U.S. PATENT DOCUMENTS

| | | | |
|---|---|---|---|
| 3,935,258 | 1/1976 | Hempel et al. | 71/120 |
| 4,315,766 | 2/1982 | Hamprecht et al. | 71/88 |

FOREIGN PATENT DOCUMENTS 1183096  9/1961  Fed. Rep. of Germany .

OTHER PUBLICATIONS

Clark, Reginald F. et al. *J. Org. Chemistry*, vol. 26 (1961) p. 5197.
Le Fave, Gene M. *J. Am. Chem. Society* vol. 71 (1949) pp. 4148–4149.
Noller, Carl R. *The Chemistry of Organic Compounds*, 2nd Ed. (1957) W. B. Saunders, Publ. p. 434.
March, Jerry *Advanced Organic Chemistry: Reactions, Mechanisms and Structure* (1968) McGraw-Hill, Publ. p. 538.

*Primary Examiner*—Paul J. Killos
*Attorney, Agent, or Firm*—James F. Tao; Arthur S. Cookfair

[57] ABSTRACT

A process for the preparation of pentahaloethoxy benzoyl halide compounds comprising
A) chlorinating p-cresyl trifluoroacetate to form p-$\alpha$, $\alpha$-dichloro-$\beta$-,$\beta$-,$\beta$-trifluoroethoxy benzotrichloride;
B) converting the p-$\alpha$, $\alpha$-dichloro-$\beta$-,$\beta$-,$\beta$-trifluoroethoxy benzotrichloride to p-pentafluoroethoxy benzoyl fluoride.

8 Claims, No Drawings

PROCESS FOR THE PREPARATION OF PENTAHALOETHOXY BENZOYL HALIDE COMPOUNDS

BACKGROUND OF THE INVENTION

This invention relates to a process for the preparation of pentafluoroethoxy benzoyl fluoride and to novel intermediates that may be employed in the process.

In recent years there have been developed a number of fluoroalkoxyphenyl-substituted compounds useful in the field of agriculture, for example as insecticides, herbicides, plant fungicides, and plant growth regulators. See for example, U.S. Pat. Nos. 3,967,949, 4,002,628 and 4,043,791, which disclose a class of fluoroalkoxyphenyl-substituted nitrogen heterocyclic compounds useful as plant growth regulators. The class of compounds disclosed includes compounds having pentafluoroethoxyphenyl substituents. The compounds prepared in accordance with the present invention are particularly useful in the synthesis of such pentafluoroethoxyphenyl-substituted compounds. Thus, for example, the pentafluoroethoxy benzoyl halide compounds of the present invention may be reacted with a suitable Grignard reagent such as isopropyl magnesium chloride, to form isopropyl p-pentafluoroethoxyphenyl ketone. The latter is disclosed in the above-cited patents as a useful reactant for the further synthesis of various pentafluoroethoxyphenyl-substituted chemical products.

SUMMARY OF THE INVENTION

In accordance with this invention there is provided a process for the preparation of p-pentafluoroethoxy benzoyl halide compounds comprising A) chlorinating p-cresyl trifluoroacetate to form p-$\alpha,\alpha$-dichloro-$\beta,\beta,\beta$,-trifluoroethoxy benzotrichloride; and B) converting the p-$\alpha,\alpha$-dichloro-$\beta,\beta,\beta$,-trifluoroethoxy benzotrichloride to p-pentafluoroethoxy benzoyl fluoride.

In another aspect, this invention relates to a series of novel and useful compounds which are readily produced as intermediates in the process, or which may be conveniently prepared from such intermediates. Among the novel compounds thus made available by means of the present process are p-$\alpha$-,$\alpha$-dichloro-$\beta$-,$\beta$-,$\beta$-trifluoroethoxy benzotrichloride (the product of step A); p-pentafluoroethoxy benzotrifluoride (produced by fluorination of the product of step A); p-trifluoroacetoxy benzotrichloride (an intermediate produced in step A); p-$\alpha$,$\alpha$-dichloro-$\beta$-,$\beta$-,$\beta$-trifluoroethoxy benzoyl chloride (produced by partial hydrolysis of the product of step A); p-$\alpha$-,$\alpha$-dichloro-$\beta$-,$\beta$-,$\beta$-trifluoroethoxy benzoic acid produced by further hydrolysis of the product of Step A.

The chlorination of p-cresyl trifluoroacetate, in accordance with step (A) above, to form p-$\alpha,\alpha$,-dichloro-$\beta,\beta,\beta$,-trifluoroethoxy benzotrichloride may be effected by reacting the p-cresyl trifluoroacetate with phosphorus pentachloride. The reaction may be illustrated by the following equation:

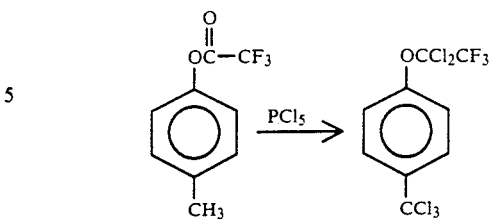

If the reaction with phosphorus pentachloride is carried out at moderate temperatures, for example in the range of 140°–150° Celsius, utilizing an approximately stoichiometric proportion of reactants, a reaction period of several days is generally necessary to achieve a substantial yield of the desired product. If the temperature is increased, for example, to greater than about 200° Celsius (under autogenous pressure) it has been found that the reaction proceeds more rapidly, but results in a difficult-to-control exothermic reaction and in the production of p-chloro-benzotrichloride as a major product and thus is somewhat less efficient. Although the mechanism is not fully understood, it may be hypothesized that the exotherm results from the rapid and preferential chlorination of the methyl group of p-trifluoroacetate by phosphorus pentachloride at the beginning of the reaction period to form p-trifluoroacetoxy benzotrichloride. At the elevated temperature, the reaction of one equivalent of phosphorus pentachloride with one equivalent of the intermediate p-trifluoroacetoxy benzotrichloride forms substantial amounts of p-chlorobenzotrichloride as an undesired side product.

It has now been found that the above-described difficulties can be in a large measure avoided in a preferred embodiment wherein the chlorination step (A) is carried out in two stages with the intermediate formation of p-trifluoroacetoxy benzotrichloride, for example, in the manner illustrated by the following equation:

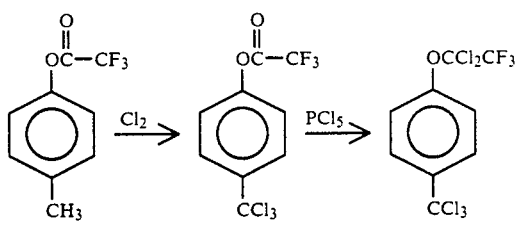

In this embodiment, it has been found preferable to first react the p-cresyl trifluoroacetate with chlorine under the influence of a free radical initiator, such as ultraviolet light, typically at temperatures in the range of about 50° to about 150° Celsius under atmospheric pressure to form p-trifluoroacetoxy benzotrichloride. The latter may then be recovered from the reaction mixture or further chlorinated, in-situ, preferably by reaction with excess PCl$_5$ at a temperature of about 50° to 250°, most preferably about 200° to about 250° Celsius to form p-$\alpha,\alpha$-dichloro-$\beta,\beta,\beta$-trifluoroethoxy benzotrichloride.

The advantages of a two stage chlorination procedure as described above include a) that the exothermic chlorination of the aromatic methyl group is moderated by the rate of addition of Cl$_2$; b) the use of less expensive Cl$_2$ in place of PCl$_5$ in the first stage is economically advantageous; c) the option of conveniently isolating and recovering the intermediate p-trifluoracetoxy benzotrichloride.

Moreover, it has been found surprisingly that: if the process temperature of the second stage of chlorination is greater than about 200° C. and preferably about 210° C. to about 250° C. and a substantial excess of PCl$_5$ is employed, for example, greater than about 2 equivalents and preferably about 4 to about 8 equivalents of PCl$_5$ per equivalent of p-trifluoroacetoxy benzotrichloride, the reaction will proceed rapidly with p-$\alpha$,$\alpha$-dichloro-$\beta$,$\beta$,$\beta$-trifluoroethoxy benzotrichloride as the major reaction product. On the other hand, if no excess of PCl$_5$ is employed, p-chlorobenzotrichloride is the major product.

The conversion of p-$\alpha$-,$\alpha$-dichloro-$\beta$-,$\beta$-,$\beta$-trifluoroethoxy benzotrichloride to p-pentafluoroethoxy benzoyl fluoride is conveniently achieved through fluorination and hydrolysis. The sequence of the fluorination and hydrolysis reactions is not critical. Thus, the p-$\alpha$-,$\alpha$-dichloro-$\beta$-,$\beta$-,$\beta$-trifluoroethoxy benzotrichloride may be first fluorinated to form p-pentafluoroethoxy benzotrifluoride (a novel compound) and the latter may then be hydrolyzed to form p-pentafluoroethoxy benzoyl fluoride. This sequence may be illustrated by the following equation:

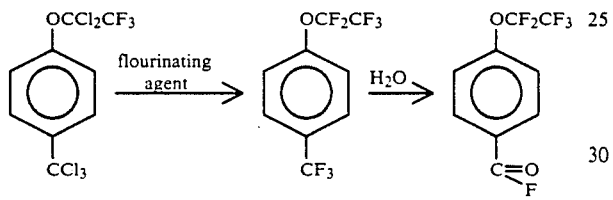

The fluorination step proceeds readily with various fluorinating agents, such as hydrogen fluoride or antimony trifluoride, at moderate temperatures, for example in the range of about 80° C. to about 200° C. Preferably the reaction is carried out at a temperature of about 90° C. to about 180° C. in the presence of a Lewis acid catalyst such as antimony pentahalide. The reaction is preferably carried out in the liquid phase at atmospheric conditions. However, if desired, super-atmospheric conditions may be employed.

The hydrolysis of the penta-fluoroethoxy benzotrifluoride intermediate to p-pentafluoroethoxy benzoyl fluoride is surprisingly facile and may be carried out by simply allowing the benzotrifluoride intermediate to react with atmospheric moisture preferably in the presence of an acid catalyst. Typically, the hydrolysis may be effected by allowing the fluorination reaction mixture, containing the pentafluoroethoxy benzotrifluoride intermediate and Lewis acid fluorination catalyst to stand for a few hours even at relatively mild conditions, such as 20° C. to 25° C., and a relative humidity of 30% to 80%. Typical acid catalysts that may be employed include, for example, Lewis acids such as antimony pentahalides, and protonic acids such as sulfuric acid and mixtures of sulfuric acid with chlorosulfonic. A particularly preferred acid catalyst is a mixture of sulfuric acid, chlorosulfonic and silica gel.

Alternatively, the sequence of fluorination and hydrolysis, respectively, may be reversed to arrive at the same end product, that is, pentafluoroethoxy benzoyl fluoride. In this manner the product of the initial chlorination step, that is p-$\alpha$-,$\alpha$-dichloro-$\beta$-,$\beta$-,$\beta$-trifluoroethoxy benzotrichloride may be hydrolyzed, for example, by reaction with a limited amount of water preferably at an elevated temperature, such as reflux temperature in the presence of a catalyst, such as ferric chloride to form p-$\alpha$-,$\alpha$-dichloro-$\beta$-,$\beta$-,$\beta$-trifluoroethoxy benzoyl chloride. The latter, may then be fluorinated, for example, by reaction with a fluorinating agent such as hydrogen fluoride, typically at a temperature in the range of about 75° C. to about 150° C., in the presence of a catalyst such as antimony pentachloride to form p-pentafluoroethoxy benzoyl fluoride. This sequence of hydrolysis followed by fluorination may be illustrated by the following equation.

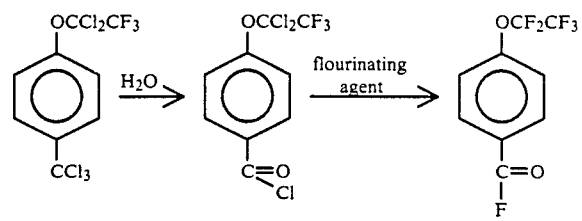

The following specific examples are provided to further illustrate this invention and the manner in which it may be carried out. It will be understood, however, that the specific details given in the examples have been chosen for purpose of illustration and are not to be construed as a limitation on the invention. In the examples, unless otherwise indicated, all parts and percentages are by weight and all temperatures are in degrees Celsius.

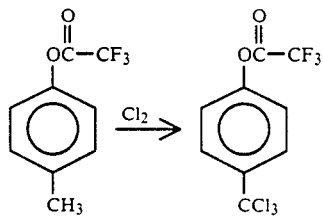

EXAMPLE 1

A portion of p-cresyl trifluoroacetate (84.9 parts) was heated to 100° C. and then irradiated with an ultraviolet lamp while an excess of chlorine was bubbled through, over a 2.5 hour period. The reaction mixture was then cooled and purged with nitrogen to yield 121 parts (94.6% yield) of p-trifluoroacetoxy benzotrichloride. Purity (determined by gas-liquid chromatography) was 99%.

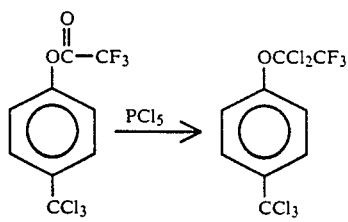

EXAMPLE 2

A) A mixture of 9.9 parts of p-trifluoroacetoxy benzotrichloride [I] and 10.4 parts of phosphorus pentachloride was heated at 180° C. (autogenous pressure) for 3 hours. The reaction mixture was analyzed via GLC.

B) The reaction mixture was heated for an additional 3 hours at 220° C. and again analyzed via GLC.

C) An additional 31.2 parts of PCl5 was added and the reaction mixture was heated at 220° C. for still another 3 hours. The reaction mixture was then analyzed via GLC.

| | RESULTS OF GLC ANALYSIS | | | |
|---|---|---|---|---|
| Step | Reactant Ratio* | Reaction Temperature (°C.) | Percent I Consumed | Product Ratio** |
| A | 1.47 | 180 | 3.9 | 10.0 |
| B | 1.47 | 220 | 10.3 | 0.83 |
| C | 4.41 | 220 | 37.4 | 6.7 |

*PCl5: p-trifluoroethoxybenzotrichloride (molar ratio)
**α, α-dichloro- β-, β-, β-trifluoroethoxy benzotrichloride p-chlorobenzotrichloride (molar ratio)

Consideration of the effects of the reaction parameters set forth in the table above, indicates that the conversion rate is improved at higher temperatures and the product ratio is improved when excess phosphorus pentachloride is employed.

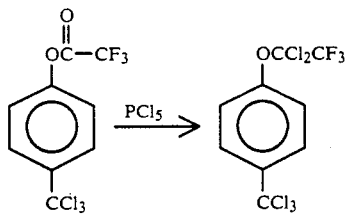

EXAMPLE 3

A mixture of 26 parts of p-trifluoroacetoxy benzotrichloride and 104 parts of phosphorus pentachloride was heated to 220° C. and maintained thereat under autogenous pressure for 5.5 hours. After separation of the excess remaining phosphorus pentachloride, the liquid reaction product was analyzed by gas-liquid chromatographic techniques with the following results (in area percent): 22.5 percent p-trifluoroacetoxy benzotrichloride; 29.1 percent p-chloro-benzotrichloride; and 48.5 percent α,α-,dichloro-β,β,-β,-trifluoroethoxy benzotrichloride.

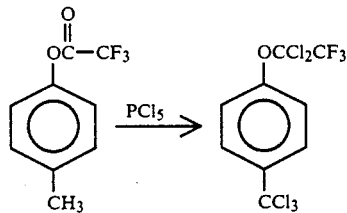

EXAMPLE 4

A mixture of 430 parts of p-cresyl trifluoroacetate and 1874 parts of phosphorus pentachloride was heated to 150° C. and maintained thereat under atmospheric pressure for 8.5 days. Acetone was added to the reaction mixture to convert excess PCl5 to POCl3 and the product was distilled to yield 576.6 parts of organic reaction mixture. The mixture was then further chlorinated by heating to 98° C. and maintaining thereat for 1.5 hours under ultra-violet radiation, while chlorine was bubbled in. Analysis of the crude reaction product indicated 21.8% p-trifluoroacetoxy benzotrichloride; 1.6% p-chloro-benzotrichloride; 74.5% α-,α-,dichloro-β,-β,-β-trifluoroethoxy benzotrifluoride; and 2.1% unidentified organic material. The crude reaction product was vacuum distilled to yield 319.7 parts of α-,α-dichloro-β,-β,-β-trifluoroethoxy benzotrichloride (b.p. 99° C./1.5 torr).

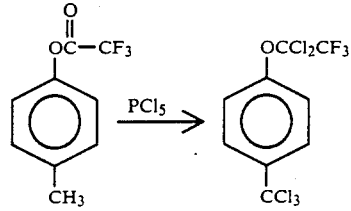

EXAMPLE 5

Phosphorus pentachloride (1714.2 parts) was added slowly, over a 6-hour period, with mixing, to 280 parts of p-cresyl-trifluoroacetate. The mixture was heated to 150° C. and maintained thereat for nine days. Acetone (214 parts) was then added to the reaction mixture to convert the excess PCl5 to POCl3, and the product was distilled to yield 229 parts of p-α,α-dichloro-β,β,β-trifluoroethoxy benzotrichloride (b.p. 115–116/2 mm; 46% yield).

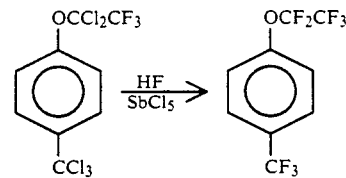

EXAMPLE 6

A mixture of 30 parts of p- α-,α-dichloro-β-,β-,βtrifluoroethoxy benzotrichloride and 3 parts of antimony pentachloride was heated to 90° C. and maintained thereat while an excess of anhydrous hydrogen fluoride was bubbled in over a 1-hour period. As excess hydrogen fluoride began to reflux, indicating substantially complete fluorination, the reaction temperature dropped to 21° C. The reaction mixture was then maintained at room temperature (about 20° C.–25° C.) while excess hydrogen fluoride was allowed to distill off over a 3-hour period. Methylene was added to the reaction mixture and the liquid portion was separated by decantation. The liquid was then treated with one part of sodium fluoride and distilled to yield 155 parts of p-pentafluoroethoxy benzotrifluoride (b.p. 136° C./1 torr.), a yield of 69%.

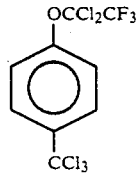

EXAMPLE 7

A mixture of 25 parts of p-α-,α-dichloro-β-,β-,β-trifluoroethoxy benzotrichloride, 35 parts of antimony trifluoride and 2 parts of antimony pentachloride was heated and maintained at 150° C. for 5 hours, then allowed to cool and remain at ambient conditions (20° C.–25° C. and about 40–60% R.H.) for about 16 hours. The reaction mixture was then distilled at about 175° C. at 1 torr. to yield 15.2 parts of p-pentafluoroethoxy benzoyl fluoride (85.4% yield).

The product of Example 7, that is p-pentafluoroethoxy benzoyl fluoride may be employed in the synthesis of isopropyl-p-pentafluoroethoxy phenyl ketone in the following manner. To a solution of p-pentafluoroethoxy benzoyl fluoride in tetrahydrofuran, at −78° C., is added one equivalent of isopropyl magnesium chloride. The reaction mixture is then acidified with 10% hydrochloric acid; extracted with diethyl ether, dried and stripped to yield isopropyl-p-pentafluoroethoxy phenyl ketone.

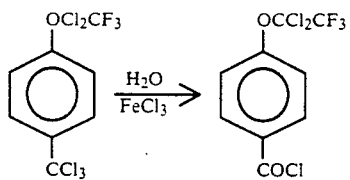

EXAMPLE 8

A mixture of 53.7 parts of p-α-,α-dichloro-β-,β-,β-trifluoroethoxy benzotrichloride, 2.7 parts of water, and 0.45 parts of ferric chloride (added incrementally) was heated to reflux and maintained thereat for about 2.5 days. The product was distilled from the reaction mixture to yield 38.3 parts of p-α-,α-dichloro-β-,β-,β-trifluoroethoxy benzoyl chloride (b.p. 123° C.–125° C./2.3 torr.; 83.3% yield).

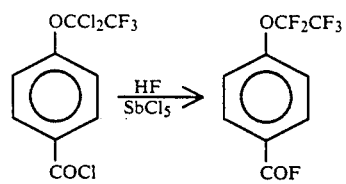

EXAMPLE 9

A mixture of 30 parts of α-,α-dichloro-β-,β-,β-trifluoroethoxy benzoyl chloride and 3 parts of antimony pentachloride was heated to 100° C. and maintained thereat while an excess of anhydrous hydrogen fluoride was bubbled into the mixture over a 4-hour period. The excess hydrogen fluoride was removed by distillation. The product was extracted with methylene chloride and the solution treated by the addition of 2 parts of sodium fluoride and 2 parts of magnesium sulfate, then filtered and concentrated to yield 13 parts of p-pentafluoroethoxy benzoyl fluoride (51% yield).

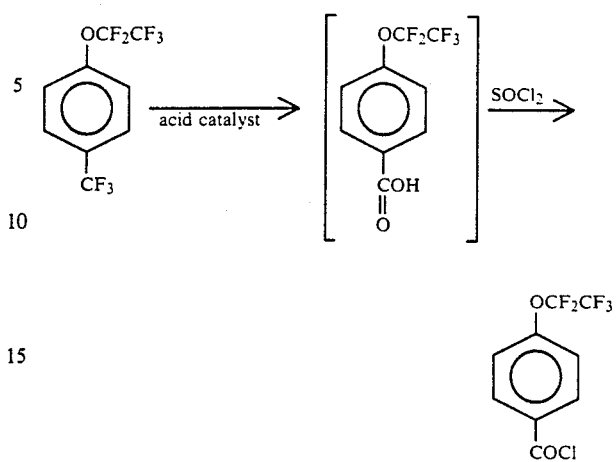

EXAMPLE 10

A mixture of 7.5 parts of p-pentafluoroethoxy benzotrifluoride, 118 parts of 98% sulfuric acid, 11 parts of chlorosulfonic acid (HSO$_3$Cl) and 2 parts of silica gel was heated to 115° C. and maintained thereat for 1.5 hours, then cooled and poured over ice. The resultant crude p-pentafluoroethoxy benzoic acid solid was mixed with 1 part of dimethyl formamide and 25 parts of thionyl chloride. The mixture was stirred for about 45 minutes and an additional 67 parts of thionyl chloride was added. The reaction mixture was then heated at reflux for 2 hours and the product distilled to yield 3.4 parts of p-pentafluoroethoxy benzoyl chloride (b.p. 152° C.–157° C.).

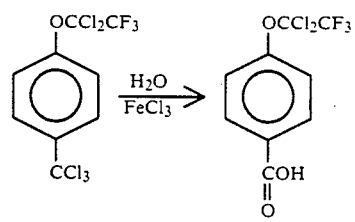

EXAMPLE 11

The compound p-α-,α-dichloro-β-,β-,β-trifluoroethoxy benzotrichloride, prepared for example, as set forth in Example 3 or 4, may be employed as a reactant in the synthesis of p-α-α-dichloro-β-,β-,β-trifluoroethoxy benzoic acid in the following manner: A mixture of 53.7 parts of p-α-,α-dichloro-β-,β-,β-trifluoroethoxy benzotrichloride, 10 or more parts of water, and 0.45 parts of ferric chloride are heated to reflux and maintained thereat for about 2.5 days. The crude reaction product is then extracted with diethyl ether, washed with 10% hydrochloric acid, dried, and evaporated to yield the desired acid product, p-α-,α-dichloro-β-,β-,βtrifluoroethoxy benzoic acid. The product is a storage stable intermediate that may be subsequently converted to the corresponding acid chloride by treatment with known chlorination reagents such as thionyl chloride, optionally in the presence of a catalyst such as dimethyl formamide.

What is claimed is:
1. A process for the preparation of pentahaloethoxy benzoyl halide compounds comprising the steps of:

(a) chlorinating p-cresyl trifluoroacetate to form p-α,α-dichloro-β-,β-,β-trifluoroethoxy benzotrichloride; and (b) (1) fluorinating the p-α,α-dichloro-β-,β-,β-trifluoroethoxy benzotrichloride to form p-pentafluoroethoxy benzotrifluoride and (2) hydrolyzing the p-pentafluoroethoxy benzotrifluoride to form p-pentafluoroethoxy benzoyl fluoride.

2. A process according to claim 1 wherein in step (b) (1), the p-α,α-dichloro-β-,β-,β-trifluoroethoxy benzotrichloride is fluorinated by reaction with a fluorinating agent in the presence of a catalyst.

3. A process according to claim 2 wherein the fluorinating agent is hydrogen fluoride.

4. A process according to claim 2 wherein the catalyst is antimony trifluoride.

5. A process according to claim 2 wherein the catalyst is antimony pentahalide.

6. A process according to claim 1 wherein in step (b) (2), the p-pentafluoroethoxy benzotrifluoride is hydrolyzed by reaction with water in the presence of an acid catalyst.

7. A process according to claim 6 wherein the acid catalyst is antimony pentahalide.

8. A process according to claim 6 wherein the acid catalyst is a mixture of sulfuric acid, chlorosulfonic acid and a silica gel.

* * * * *